(12) United States Patent
Harling et al.

(10) Patent No.: US 6,277,861 B1
(45) Date of Patent: Aug. 21, 2001

(54) ANTI-CONVULSANT ISOQUINOLYL-BENZAMIDE DERIVATIVES

(75) Inventors: John David Harling, Sawbridgeworth; Barry Sidney Orlek, Epping; Mervyn Thompson, Harlow, all of (GB)

(73) Assignee: SmithKline Beecham, p.l.c., Brentford (GB)

( * ) Notice: Subject to any disclaimer, the term of this patent is extended or adjusted under 35 U.S.C. 154(b) by 0 days.

(21) Appl. No.: 09/381,369

(22) PCT Filed: Mar. 16, 1998

(86) PCT No.: PCT/GB98/00781
§ 371 Date: Dec. 21, 1999
§ 102(e) Date: Dec. 21, 1999

(87) PCT Pub. No.: WO98/41507
PCT Pub. Date: Sep. 24, 1998

(30) Foreign Application Priority Data

Mar. 18, 1997 (GB) .................................................. 9705620
Dec. 17, 1997 (GB) .................................................. 9726660

(51) Int. Cl.[7] ........................ A61K 31/47; C07D 215/46; C07D 215/38
(52) U.S. Cl. ........................... 514/310; 546/165; 546/171
(58) Field of Search .................................. 546/165, 171; 514/310

(56) References Cited

U.S. PATENT DOCUMENTS 4,022,900 * 5/1977 Mathison .

FOREIGN PATENT DOCUMENTS

0266949 * 5/1988 (EP) .
0366228 * 10/1989 (EP) .
WO 9222293 * 12/1992 (WO) .
WO 9748683 * 12/1997 (WO) .

OTHER PUBLICATIONS

Fries, et al., "0–Divinylbenzene and napthalene", (1938), Chemical Abstracts, vol. 32, No. 5, XP002065867; & Ann. (1937), 533, pp. 72–92.

* cited by examiner

Primary Examiner—D. Margaret Seaman
(74) Attorney, Agent, or Firm—Linda E. Hall; Stephen A. Venetianer; Charles M. Kinzig

(57) ABSTRACT

Compounds of formula (I) and pharmaceutically acceptable salts thereof, where $R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—; $R^2$ is hydrogen or up to three substituents selected from halogen, $NO_2$, CN, $N_3$, $CF_3O$—, $CF_3S$—, $CF_3CO$—, trifluoromethyldiazirinyl, $C_{1-6}$?alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl$)$NHSO$_2$—, $(C_{1-4}$alkyl$)_2$NCO—, $(C_{1-4}$alkyl$)$NHCO— or $CONH_2$; or —$NR^5R^6$ where $R^5$ is hydrogen or $C_{1-4}$alkyl, and $R^6$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and the two $R^3$ groups and the two $R^4$ groups are each independently hydrogen or $C_{1-6}$alkyl or the two $R^3$ groups and/or the two $R^4$ groups together form a $C_{3-6}$spiroalkyl group provided that at least one $R^3$ and $R^4$ group is not hydrogen, are useful in the treatment and prophylaxis of epilepsy and other disorders.

(I)

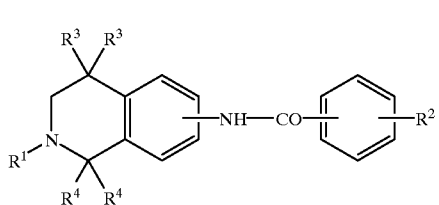

20 Claims, No Drawings

ANTI-CONVULSANT ISOQUINOLYL-BENZAMIDE DERIVATIVES

This invention relates to novel compounds, to processes for preparing them, and to their use as therapeutic agents. U.S. Pat. No. 4,022,900 (Marion) discloses benzamido-tetrahydroisoquinolines having anti-hypertensive and vasodilator properties.

WO97/48683 (Smithline Beecham), unpublished at the filing date of this application, discloses that benzamide compounds of formula (A) below possess anticonvulsant activity and are therefore believed to be useful in the treatment and/or prevention of anxiety, mania, and related depression disorders.

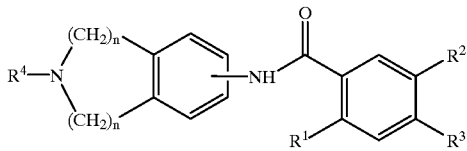

(A)

where n and p are independently integers from 1 to 4 and (n+p) is from 2 to 5;

$R^1$ is $C_{1-6}$alkylO—;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$— or $(C_{1-4}$alkyl)NHSO$_2$—;

$R^3$ is hydrogen, halogen, NO$_2$, CN, $N_3$, trifluoromethyldiazirinyl, $C_{1-6}$ alkylO—, $C_{1-6}$ alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —NR$^5$R$^6$ where R$^5$ is hydrogen or $C_{1-4}$ alkyl, and R$^6$ is hydrogen, $C_{1-4}$alkyl, —CHO, —CO$_2$C$_{1-4}$alkyl or —COC$_{1-4}$alkyl;

$R^4$ is hydrogen, $C_{1-6}$ alkyl, $C_{1-6}$ alkenyl, or $C_{1-6}$ alkynyl.

It has now been surprisingly found that carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tirmitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Accordingly, the present invention provides a compound of formula (I) or pharmaceutically acceptable salt thereof:

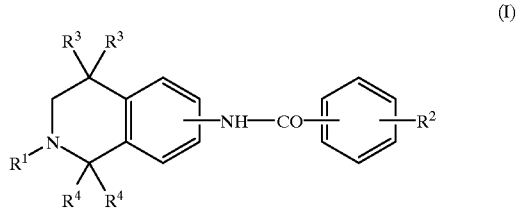

(I)

where $R^1$ is hydrogen, $C_{1-6}$ alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—, $R^2$ is hydrogen or up to three substituents selected from halogen, NO$_2$, CN, N$_3$, CF$_3$O—, CF$_3$S—, CF$_3$CO—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl)NHSO$_2$—, $(C_{1-4}$alkyl$)_2$NCO—, $(C_{1-4}$alkyl)NHCO— or CONH$_2$;

or —NR$^5$R$^6$ where R$^5$ is hydrogen or $C_{1-4}$ alkyl, and R$^6$ is hydrogen, $C_{1-4}$alkyl, formyl, —CO$_2$C$_{1-4}$alkyl or —COC$_{1-4}$alkyl;

or two R$^2$ groups together form a carbocyclic ring that is saturated or unsaturated and unsubstituted or substituted by —OH or =O; and the two R$^3$ groups and the two R$^4$ groups are each independently hydrogen or $C_{1-6}$ alkyl or the two R$^3$ groups and/or the two R$^4$ groups together form a $C_{3-6}$ spiroalkyl group provided that at least one R$^3$ and R$^4$ group is not hydrogen.

The compounds of this invention are typically isoquinolinyl-carboxamides, especially (tetrahydroisoquinolin-7-yl)carboxamides. The carboxamide moiety may be a benzamide. When two R$^2$ groups form a carbocyclic ring, this is typically a 5–7 membered ring, and the carboxamide moiety may be a naphthalene carboxamide or an indane or indanone carboxamide.

In the formula (I), alkyl groups, including alkyl groups that are part of other moieties, such as alkoxy or acyl, may be straight chain or branched. Phenyl groups, including phenyl groups that are part of other moieties, in R$^2$ may optionally be substituted with one or more independently selected halogen or $C_{1-6}$ alkyl, $C_{1-6}$ alkoxy or $C_{1-6}$ alkylcarbonyl. Suitable $C_{3-6}$ cycloalkyl groups include cyclopropyl, cyclobutyl, cyclopentyl, and cyclohexyl. Suitable halo substituents include fluoro, chloro, iodo and bromo.

It should be appreciated that compounds of the present invention possess chiral centres and as such may exist in different enantiomeric forms, the present invention extends to each enantiomeric form and mixtures thereof including diastereoisomers and racemates.

One suitable group of compounds of this invention are of formula (IA)

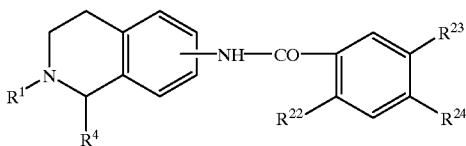

(IA)

where
R¹ is hydrogen, C₁₋₆ alkyl (optionally substituted by hydroxy or C₁₋₄alkoxy), C₁₋₆ alkenyl, C₁₋₆ alkynyl, formyl, C₁₋₆alkylCO, C₁₋₆alkylSO₂, or CF₃CO—;

R²² is C₁₋₆alkylO—, C₃₋₆cycloalkylO— or C₃₋₆cycloalkyl C₁₋₄alkylO—;

R²³ is hydrogen, halogen, CN, N₃, trifluoromethyldiazirinyl, C₁₋₆perfluoroalkyl, CF₃O—, CF₃S—, CF₃CO—, C₁₋₆alkyl, C₃₋₆cycloalkyl, C₃₋₆cycloalkyl-C₁₋₄alkyl-, C₁₋₆alkylO—, C₁₋₆alkylCO—, C₃₋₆cycloalkylCO—, C₃₋₆cycloalkyl-C₁₋₄alkylCO—, phenyl, phenoxy, benzyloxy, benzoyl, phenyl-C₁₋₄alkyl-, C₁₋₆alkylS—, C₁₋₆alkylSO₂—, (C₁₋₄alkyl)₂NSO₂, (C₁₋₄alkyl)NHSO₂, (C₁₋₄alkyl)₂NCO—, (C₁₋₄alkyl)NHCO— or CONH₂;

R²⁴ is hydrogen, halogen, NO₂, CN, N₃, trifluoromethyldiazirinyl, C₁₋₆ alkylO—, C₁₋₆ alkylS—, C₁₋₆ alkyl, C₃₋₆cycloalkyl, C₃₋₆cycloalkyl-C₁₋₄alkyl-, C₁₋₆alkenyl, C₁₋₆alkynyl, CF₃CO—, C₁₋₆alkylCO—, C₃₋₆cycloalkylCO—, C₃₋₆cycloalkyl-C₁₋₄alkylCO—, phenyl, phenoxy, benzyloxy, benzoyl, phenylC₁₋₄alkyl-;

or —NR⁵R⁶ where R⁵ is hydrogen or C₁₋₄ alkyl, and R⁶ is hydrogen, C₁₋₄alkyl, formyl, —CO₂C₁₋₄alkyl or —COC₁₋₄alkyl;

or R²³ and R²⁴ together form a carbocyclic ring that is unsaturated or saturated and unsubstituted or substituted by carbonyl or hydroxyl;

R⁴ is C₁₋₆ alkyl.

Another suitable group is of formula (IB)

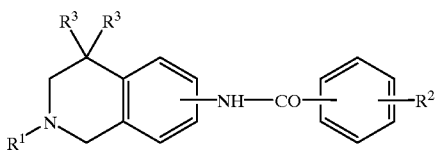

(IB)

where R¹ is hydrogen, C₁₋₆ alkyl (optionally substituted by hydroxy or C₁₋₄alkoxy), C₁₋₆alkenyl, C₁₋₆alkynyl, C₁₋₆alkylCO—, formyl, CF₃CO— or C₁₋₆alkylSO₂—, R² is hydrogen or up to three substituents selected from halogen, NO₂, CN, N₃, CF₃O—, CF₃S—, CF₃CO—, trifluoromethyldiazirinyl, C₁₋₆alkyl, C₁₋₆alkenyl, C₁₋₆alkynyl, C₁₋₆perfluoroalkyl, C₃₋₆cycloalkyl, C₃₋₆cycloalky-C₁₋₄alkyl-, C₁₋₆alkylO—, C₁₋₆alkylCO—, C₃₋₆cycloalkylO—, C₃₋₆cycloalkylCO—, C₃₋₆cycloalkyl-C₁₋₄alkylO—, C₃₋₆cycloalkyl-C₁₋₄alkylCO—, phenyl, phenoxy, benzyloxy, benzoyl, phenyl-C₁₋₄alkyl-, C₁₋₆alkylS—, C₁₋₆alkylSO₂—, (C₁₋₄alkyl)₂NSO₂—, (C₁₋₄alkyl)NHSO₂—, (C₁₋₄alkyl)₂NCO—, (C₁₋₄alkyl)NHCO— or CONH₂;

or —NR⁵R⁶ where R⁵ is hydrogen or C₁₋₄ alkyl, and R⁶ is hydrogen, C₁₋₄alkyl, formyl, —CO₂C₁₋₄alkyl or —COC₁₋₄alkyl;

or two R² groups together form a cabocyclic ring that is saturated or unsaturated and unsubstituted or substituted by —OH or =O; and each R³ is C₁₋₆ alkyl.

A further suitable group is of formula (IC)

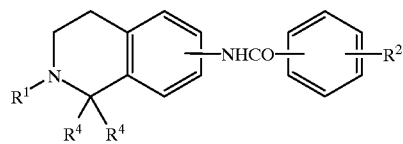

(IC)

where R¹ is hydrogen, C₁₋₆ alkyl (optionally substituted by hydroxy or C₁₋₄alkoxy), C₁₋₆alkenyl, C₁₋₆alkynyl, C₁₋₆alkylCO—, formyl, CF₃CO— or C₁₋₆alkylSO₂—, R² is hydrogen or up to three substituents selected from halogen, NO₂, CN, N₃, CF₃O—, CF₃S—, CF₃CO—, trifluoromethyldiazirinyl, C₁₋₆alkyl, C₁₋₆alkenyl, C₁₋₆alkynyl, C₁₋₆perfluoroalkyl, C₃₋₆cycloalkyl, C₃₋₆cycloalkyl-C₁₋₄alkyl-, C₁₋₆alkylO—, C₁₋₆alkylCO—, C₃₋₆cycloalkylO—, C₃₋₆cycloalkylCO—, C₃₋₆cycloalkyl-C₁₋₄alkylO—, C₃₋₆cycloalkyl-C₁₋₄alkylCO—, phenyl, phenoxy, benzyloxy, benzoyl, phenyl-C₁₋₄alkyl-, C₁₋₆alkylS—, C₁₋₆alkylSO₂—, (C₁₋₄alkyl)₂NSO₂—, (C₁₋₄alkyl)NHSO₂—, (C₁₋₄alkyl)₂NCO—, (C₁₋₄alkyl)NHCO— or CONH₂;

or —NR⁵R⁶ where R⁵ is hydrogen or C₁₋₄ alkyl, and R⁶ is hydrogen, C₁₋₄alkyl, formyl, —CO₂C₁₋₄alkyl or —COC₁₋₄alkyl;

or two R² groups together form a carbocyclic ring that is saturated or unsaturated and unsubstituted or substituted by —OH or =O; and each R⁴ is C₁₋₆ alkyl.

A suitable group of compounds of formula (I), (IB) and (IC) have

R¹ as hydrogen, methyl, ethyl, propyl, hydroxyethyl, methoxyethyl, formyl, acetyl, trifluoroacetyl or methanesulfonyl, R² as hydrogen or one or more of methyl, ethyl, n-butyl, iso-propyl, t-butyl, phenyl, methoxy, ethoxy, iso-propoxy, cyclopropylmethoxy, n-butoxy, phenoxy, benzyloxy, amino, acetylamino, nitro, azido, cyano, bromo, chloro, fluoro, iodo, acetyl, pivaloyl, iso-butyroyl, benzoyl, iodobenzoyl, trifluoromethyl, perfluoroethyl, trifluoromethoxy, trifluoroacetyl, methanesulfonyl, n-propylsulfonyl, isopropylsulfonyl, dimethylsulfamoyl, R³ one or both is methyl, R⁴ one or both is methyl.

In compounds of formula (IA) groups R¹ and R⁴ are suitably selected from the above list, and R²², R²³ and R²⁴ are selected as appropriate values from the above listing for R².

A preferred group of compounds of formula (I) have

R¹ as hydrogen, methyl, ethyl,

R² as hydrogen or one or more of methyl, ethyl, i-propyl, t-butyl, methoxy, ethoxy, i-propoxy, bromo, chloro, cyano, trifluoromethyl, R³ one or both is methyl, R⁴ one or both is methyl.

Examples of compounds of formula (I) are:

(±) N-(1-methyl-1,2,3,4-tetrahydroisoquinolin-5-yl)-5-chloro-4-ethoxy-2-methoxybenzamide (±) N-(1,2-dimethyl-1,2,3,4-tetrahydroisoquinolin-5-yl)-5-bromo-2,4-dimethoxybenzamide (±) N-(1,2-dimethyl-1,2,3,4-tetrahydroisoquinolin-5-yl)-5-chloro-4-ethoxy-2-methoxybenzamide (±) N-(1,2-dimethyl-1,2,3,4-tetrahydroisoquinolin-5-yl)-5-chloro-4-iso-propoxy-2-methoxybenzamide (±) N-(1,2-dimethyl-1,2,3,4-tetrahydroisoquinolin-5-yl)-4-tert-butyl-2-methoxybenzamide (±) N-(1,2-dimethyl-1,2,3,4-tetrahydroisoquinolin-5-yl)-5-trifluoromethyl-2-methoxy-4-methyl-benzamide N-(2,4,4-trimethyl-4H-isoquinolin-7-yl)-4-methoxy-3-trifluoromethylbenzamide N-(2,4,4-trimethyl-4H-isoquinolin-7-yl)-3-cyano-4-iso-propylbenzamide N-(2,4,4,-trimethyl-4H-isoquinolin-7-yl)-3-bromo-4-ethylbenzamide N-(2,4,4-trimethyl-4H-isoquinolin-7-yl)-3-bromo-4-ethoxybenzamide N-(2,4,4-trimethyl-4H-isoquinolin-7-yl)-3-chloro-4-iso-propoxybenzamide (±) N-(1,2-dimethyl-4H-isoquinolin-7-yl)-3-bromo-4-ethylbenzamide (±) N-(1,2-dimethyl-4H-isoquinolin-7-yl)-3-bromo-4-ethoxybenzamide N-(1,1,2-trimethyl-4H-isoquinolin-7-yl)-4-methoxy-3-trifluoromethylbenzamide When synthesised, these compounds are often in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sublingual, nasal, rectal, topical or transdermal administration.

An amount effective to treat the disorders hereinbefore described depends on the usual factors such as the nature and severity of the disorders being treated and the weight of the mammal However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of filers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits aosociated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Another aspect of the invention is a process for the preparation of compounds of formula (II) (I) as herein before described which comprises reacting a compound of formula (II)

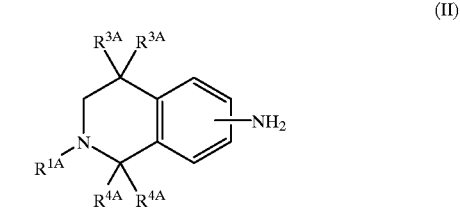

(II)

where $R^{1A}$, $R^{3A}$, $R^{4A}$ are $R^1$, $R^3$, $R^4$ as defined for formula (I) or a group or groups convertible to $R^1$, $R^3$, $R^4$ with a compound of formula (III)

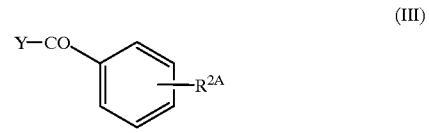

(III)

where Y is Cl or OH, and $R^{2A}$ groups are independently $R^2$ as defined for formula (I) or a group or groups convertible to $R^2$, and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

Reaction of a compound of formula (III) which is a benzoyl chloride derivative (Y=Cl) will lead directly to the hydrochloride Sal Suitable solvents include ethyl acetate or dichloromethane, optionally in the presence of a base such as triethylamine. When the compound of formula (III) is a benzoic acid derivative (Y=OH), conventional conditions for condensation of aromatic acids with amines may be used, for example reacting the components in a mixture of ethyl-(dimethylaminopropyl)-carbodiimide/hydroxybenzotriazole in a suitable inert solvent such as dimethyl formamide.

Conversions of an $R^{1A}$, $R^{2A}$, $R^{3A}$, $R^{4A}$ group to a $R^1$, $R^2$, $R^3$, $R^4$ group typically arise when a protecting group is needed during the above coupling reaction or during the preparation of the reactants by the procedures described below. Interconversion of one $R^1$, $R^2$, $R^3$, $R^4$ group to another typically arises when one compound of formula (I) is used as the immediate precursor of another compound of formula (I) or when it is easier to introduce a more complex or reactive substituent at the end of a synthetic sequence.

Compounds of formula (II) when $R^4$=H or alkyl may be prepared from the corresponding isoguinoline of formula (IV)

(IV)

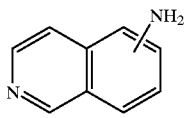

by reaction with a compound $R^{1A}Z$ where Z is a leaving group such as halogen, especially iodo, or tosylate to obtain an intermediate of formula (V)

(V)

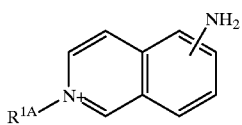

which is reacted with an $R^{4A}$ containing Grignard reagent under conventional conditions to obtain a dihydroisoquinoline of formula (VI)

(VI)

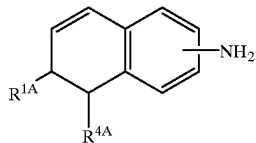

which can be hydrogenated, for example using hydrogen and a palladium/activated carbon catalyst, to obtain a tetrahydroisoquinoline of formula (II) which is a precursor for compounds of formula (IA).

Alternatively the compound of formula (IV) may be a nitro-isoquinoline, and the nitro group is converted to an amino group in the hydrogenation step.

When the intended $R^1$ is hydrogen, the N of the isoquinoline is preferably protected conventionally, for example by making $R^{1A}$ benzyl, or 4-methoxybenzyl during introduction of the $R^4$ group via the Grignard reagent. Again protection is preferably provided prior to formation of the benzamide, for example by tert.-butoxycarbonyl and then deprotected under standard conditions, for example using trifluoroacetic acid/methylene chloride.

Amino/nitro-isoquinolines of formulae (IV) and the reagents used are commercially available, or can be prepared from commercially available materials using conventional procedures described in the literature (eg. I. W. Matheson et al, J. Med. Chem. 1973, 16, 332).

Compounds of formula (II) which are precursors for compounds of formula (IB) may be prepared from the corresponding nitro-isoquinoline dione of formula (VW) with di-$R^3$ substitution, by converting the nitro group to amino by catalytic hydrogenation as above and subsequently removing the dione groups by reduction with diborane. The nitro-dione may be obtained by treating a di-$R^3$isoquinoline dione [prepared using the procedure of H. Takechi et al., Synthesis. 1992, 778] with fuming nitric acid. $R^{1A}$ groups may be introduced as described above.

(VII)

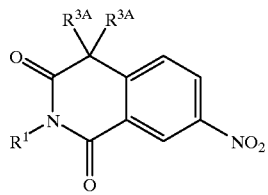

Compounds of formula (II) which are precursors for compounds of formula (IC) may be prepared from the corresponding nitro-3,4-dihydroisoquinoline by reduction with tin (II) chloride to the amino compound followed by quaternisation with an $R^{1A}$-X halide and subsequent treatment with an $R^4$ Grignard reagent. Compounds of formula (II) where both $R_4$ are alkyl may be prepared from the corresponding 1-alkyl-3,4-dihydroisoquinoline by nitration [using procedures by R. D. Larsen et al, J. Org. Chem., 1991 56 6034 and A. P. Venkov and S. S. Abeghe, Syn. Commun., 1996 26 127] followed by quaternisation and treatment with an $R^4$ Grignard reagent as described above.

Compounds of formula (III) may be prepared by further substitution of commercially available benzoic acid derivatives using conventional procedures, or by oxidation of corresponding substituted benzyl alcohols. Alternatively benzoic acids can be prepared from correpondingly substituted phenols, for example by formation of the acetate, conversion to an acetophenone and then to the desired acid.

Where the above described intermediates are novel compounds, they also form part of this invention.

The preparation of compounds of ftis invention is further illustrated by the following Preparations, Descriptions and Examples. The utility of compounds of this invention is shown by the Pharmacological Data that follow the Examples.

DESCRIPTION 1

(±) 5-Amino-2-benzyl-1-methyl-1,2-dihydroisoquinoline

To solution of 5-aminoisoquinoline (15 g, 104 mmol) in acetone (400 ml) was added benzyl bromide (18.6 ml, 156 mmol). The mixture was stirred at room temp for 2 h before the precipitate was filtered off affording an orange solid (8.64 g). A second crop (4.02 g) was filtered after a further 2 h. To a solution of this 5-amino-2-benzyl-isoquinolinium bromide (8.46 g, 26.8 mmol) in THF (75 ml) at 0° C. under argon was added dropwise methyl magnesium chloride (17.89 ml, 56.6 mmol). The mixture was allowed to warm up to room temperature and was stirred for 2 h. The mixture was then poured into ammonium chloride solution and extracted with ether. The organic layer was dried over sodium sulfate and concentrated in vacuo to afford the title compound as a light brown solid (5.0 g).

DESCRIPTION 2

(±) 5-Amino-1-methyl-1,2,3,4-tetrahydroisoquinoline

5-Amino-2-benzyl-1-methyl-1,2-dihydroisoquinoline (4.5 g, 17.9 mmol) was dissolved in ethanol (250 ml); 10% palladium catalyst on activated carbon (1 g) was then added and the mixture hydrogenated at atmospheric pressure for 24 h. The catalyst was then removed by filtration through Kieselguhr and the solvent removed in vacuo to afford a brown solid. This residue was then subjected to column chromatography eluting with 5 to 10% methanol-dichloromethane. The relevant fractions were combined and concentrated in vacuo to afford a brown solid (1.26 g).

DESCRIPTION 3

(±) 5-Amino-2-(t-butoxycarbonyl)-1-methyl-1,2,3,4-tetrahydroisoquinoline

5-Amino-1-methyl-1,2,3,4-tetrahydroisoquinoline (0.39 g, 2.4 mmol) was dissolved in 1,4-dioxane (25 ml) and sodium hydroxide solution (3M, 0.8 ml) and cooled in an ice bath. The di-t-butyldicarbonate (0.53 g, 2.4 mmol) was added and the mixture stirred at room temp for 2 h. The mixture was then poured into water and extracted with ether. The organic layer was dried over sodium sulfate and concentrated in vacuo to afford a white solid. (0.251 g).

DESCRIPTION 4

(±) 5-Amino-1,2-dihydro-1,2-dimethylisoquinoline

5-Aminoisoquinoline (25 g, 173 mmol) was dissolved in acetone (500 ml) and methyl iodide (25 ml, 410 mmol) was added. After stirring at room temperature for 1 h the orange precipitate was filtered off, washed with acetone and dried in vacuo, affording an orange solid (40.3 g). A second crop was filtered off after 2 h affording an orange solid (0.84 g). To a solution of this 5-amino-2-methylisoqwnolinium iodide (21.013 g, 73.19 mmol) in THF (150 ml) at 0° C. under argon was added methyl magnesium chloride (36.6 ml 109.8 mmol) dropwise. The mixture was allowed to stir at room temperature for 2 h before being poured into ammonium chloride and extracted with ether. The organic layer was dried over sodium sulfate and concentrated in vacuo to afford a dark brown oil (8.52 g).

DESCRIPTION 5

(±) 5-Amino-1,2-dimethyl-1,2,3,4-tetrahydroisoquinoline

To an ice cold solution of 5-amino-1,2-dihydro-1,2-dimethyl isoquinoline (4 g, 23.2 mmol) in methanol (80 ml) was added sodium borohydride (3.51 g, 92.8 mmol) portionwise. The mixture was allowed to stir at room temperature overnight before concentration in vacuo; the residue was then partitioned between water and dichloromethane. The organic layer was dried over sodium sulfate and concentrated in vacuo to afford a light brown oil (4.023 g).

DESCRIPTION 6

7-Nitro-2,4,4-trimethyl-4H-isoquinoline-1,3-dione 2,4,4-Trimethyl-4H-isoquinoline-1,3-dione (5 g, 24.6 mmol) [prepared according to H. Takechi et al., Synthesis. 1992, 778] was dissolved in concentrated sulfuric acid (50 ml) at 0° C. Fuming nitric acid (2.5 ml) was added dropwise over 5 min and the reaction warmed to 25° C. After stirring for 30 min at 25° C. the reaction mixture was poured into ice water (100 ml) and the organics extracted into dichloromethane (3×50 ml). The combined organic extracts were dried over magnesium sulfate and evaporated in vacuo to give the title compound (5.31 g, 86%).

$^1$H NMR (250 MHz, CDCl$_3$) δ: 1.70 (6H, s), 3.42 (3H, s), 7.69 (1H, d, J=9 Hz), 8.46 (1H, dd, J=9, 2 Hz), 9.07 (1H, d, J=2 Hz); m/z (API$^+$): 249 (M+H)$^+$

DESCRIPTION 7

7-Amino-2,4,4,-trimethyl-4H-isoquinoline-1,3-dione

7-Nitro-2,4,4-trimethyl-4H-isoquinoline-1,3-dione (45 g, 20 mmol) was dissolved in a methanol (500 ml)/dichloromethane (100 ml) mixture and treated with 10% Pd/C (0.5 g). The reaction mixture was hydrogenated for 2 h before removal of the palladium catalyst by filtration through Celite. The filtrate was evaporated to dryness in vacuo to give the title compound (4.4 g, quant).

$^1$H NMR (250 MHz, CDCl$_3$) δ: 1.58 (6H, s), 3.36 (3H, s), 3.83 (2H, brs), 6.95 (1H, dd,J=6, 3 Hz), 7.24 (1H, d, J=6 Hz), 7.48 (1H, d, J=3 Hz); m/z (API$^+$): 219 (M+H)$^+$

DESCRIPTION 8

7-Amino-2,4,4-trimethyl-4H-isoquinoline, hydrochloride

7-Amino-2,4,4-trimethyl-4H-isoquinoline-1,3-dione (4 g, 18.3 mmol) was dissolved in tetrahydrofuran (400 ml) and heated at reflux (~61° C.). Borone-tetrahydrofuran complex (88 ml, 1M solution in THF) was added dropwise to the mixture and heating continued for a further 3 h. The cooled reaction (0° C.) was treated with methanol (400 ml) dropwise to destroy residual borane, followed by evaporation in vacuo. The resultant residue was heated at reflux in 3N HCl (400 ml) for 30 min. The mixture was cooled to 0° C. and treated with NaOH pellets until basic (pH 9). The free amine was extracted into dichloromethane (4×100 ml) before drying over magnesium sulfate and evaporation in vacuo. The resulting light brown oil was dissolved in dichloromethane (50 ml) and treated with hydrogen chloride (1M solution in ether) until acidic (pH 2). Solvent removal in vacuo followed by trituration with ether yielded the title compound as an off-white powder (3.3 g, 79%).

$^1$H NMR (free base 250 MHz, CDCl$_3$) δ: 1.25 (6H, s), 2.37 (2H, s), 2.39 (3H, s), 3.43 (2H, s), 3.51 (2H, brs), 6.32 (1H, d, J=2 Hz), 6.54 (1H, dd, J=8, 2 Hz), 7.09 (1H, d, J=8 Hz); m/z (API$^+$): 191 (M+H)$^+$

DESCRIPTION 9

7-Anino-3,4-dihydroisoquinoline

7-Nitro-3,4-dihydroisoquinoline (0.60 g, 3.4 mmol) [prepared according to the procedure of A. P. Venkov et al, Syn. Commun., 1996 26 127] was dissolved in ethanol (100 ml) and heated to 60° C. This hot solution was treated with a solution of tin (II) chloride dihydrate (3.08 g, 13.7 mmol) in conc. HCl (10 ml). The resultant mixture was heated at 60° for 1 h. Upon cooling, the reaction mixture was poured into water (100 ml) and basified (pH 9) with KOH pellets, liberating an oily residue. This residue was extracted into dichloromethane and dried over magnesium sulfate. Purification by chromatography through silica gel, eluting with (0.5% conc. ammonia: 4.5% methanol: 95% dichloromethane) yielded the title compound as a dark yellow oil (0.44 g, 88%).

$^1$H NMR (250 MHz, CDCl$_3$) δ: 2.63 (2H, t, J=7 Hz), 3.67 (2H, brs), 3.73 (2H, dt, J=7, 2 Hz), 6.62 (1H, d, J=2 Hz), 6.70 (1H, dd, J=8, 2 Hz), 6.95 (1H, d, J=8 Hz), 8.24 (1H, s); m/z (API): 147 (M+H)$^+$, 148 (M+2H)$^{2+}$

DESCRIPTION 10

7-Amino-2-methyl-3,4-dihydroisoquinolinium iodide 7-amino-3,4-dihydroisoquinoline (0.40 g, 2.74 mmol) in acetone (125 ml) was treated with iodomethane (0.50 ml, 8.03 mmol) and left stirring at room temperature for 18 h. The resultant yellow precipitate was collected by filtration and dried in vacuo at ambient temperature (0.73 g, 92%). m/z (API)=161 (M)$^+$

DESCRIPTION 11

(±) 7-Amino-1,2-dimethyl-tetrahydroisoquinoline (±) 7-Amino-2-methyl-3,4-dichloroisoquinolinium iodide (0.50 g, 1.7 mmol) was suspended in anhydrous tetrahydrofuran (50 ml) and cooled to −78° C. The cooled solution was treated with methyl magnesium chloride (2.14 ml of a 3M solution in THF, 6.96 mmol), added as a single portion. The reaction was allowed to reach room temperature over 18 h before being poured into water (50 ml). The organic solvent was removed in vacuo and the organic product extracted into dichloromethane. Drying over magnesium sulfate and evaporation in vacuo fuinished the title compound as a pale yellow oil (0.3 g, 98%). For ease of handling the product was converted into a monohydrochloride.

$^1$H NMR (250 MHz, CDCl$_3$) δ: 1.37 (3H, d, J=7 Hz), 2.46 (3H, s), 2.54–2.83 (3H, m), 3.00 (1H, m), 3.50 (3H, m), 6.45 (1H, d, J=2 Hz), 6.51 (1H, dd, J=8, 2 Hz), 6.88 (1H, d, J=8 Hz); m/z, (API): 177 (M+H)$^+$

DESCRIPTION 12

(±) 1-Methyl-7-nitro-3,4-dihydroisoquinoline

A solution of (±) 1-methyl-3,4-dihydroisoquinoline (2.57 g, 17.7 mmol) in conc. sulfuric acid (10 ml) was added dropwise to a stirred mixture of potassium nitrate (1.93 g, 19.1 mmol) in conc. sulfuric acid (10 ml) at −5° C. The mixture was allowed to reach room temperature over 2 h and then heated at 60° C. for 4 h. The reaction mixture was poured into ice-water (100 ml) and basified (pH 9) with KOH pellets. Extraction into dichloromethane (3×50 ml), drying over anhydrous sodium sulfate and evaporation in vacuo yielded the crude product. Purification by chromatography through silica gel, eluting with (0.5% 0.88 NH$_3$: 4.5% CH$_3$OH: 95% CH$_2$Cl$_2$) afforded the title compound as a dark brown oil (1.92 g, 57%).

$^1$H NMR (250 MHz, CDCl$_3$) δ: 2.48 (3H, s), 2.82 (2H, t, J=8 Hz), 3.75 (2H, dt, J=8, 1 Hz), 7.38 (1H, d, J=8 Hz), 8.24 (1H, dd, J=8, 2 Hz), 8.33 (1H, d, J=2 Hz). m/z (API): 191 (M+H)$^+$

DESCRIPTION 13

(±) 7-Amino-1-methyl-3,4-dihydroisoquinoline (±) 1-Methyl-7-nitro-3,4-dihydroisoquinoline (2.0 g, 10.5 mmol) was dissolved in ethanol (150 ml) and heated to 60° C., before treatment with a solution of tin (II) chloride dihydrate (9.5 g, 42.1 mmol) in conc. HCl (30 ml). The resultant mixture was heated at 60° C. for 1 h. After cooling, the reaction mixture was poured into water (200 ml) and basified (pH 9) with KOH pellets, liberating an oily residue. This residue was extracted into dichloromethane and dried over magnesium sulfate. Purification by chromatography through silica gel, eluting with (0.5% 0.88 NH$_3$: 4.5% CH$_3$OH: 95% CH$_2$Cl$_2$) yielded the title compound as a dark brown oil (0.93 g, 55%).

$^1$H NMR (250 MHz, CDCl$_3$) δ: 2.35 (3H, s), 2.59 (2H, t, J=7 Hz), 3.62 (2H, t, J=7 Hz), 3.60 (2H, brs), 6.71 (1H, dd, J=8, 2 Hz), 6.83 (1H, d, J=2 Hz), 6.98 (1H, d, J=8 Hz).

DESCRIPTION 14

(±) 7-Amino-1,2-dimethyl-3,4-dihydroisoquinolinium iodide (±) 7-Amino-1-methyl-3,4-dihydroisoquinoline (0.90 g, 5.6 mmol) in acetone (125 ml) and iodomethane (1.0 ml, 16 mmol) was stirrd at room temperature for 18 h. The resultant precipitate was collected by filtration and dried in vacuo at ambient temperature. The title compound was isolated as an orange powder (1.44 g, 85%). m/z (API): 175 (M)$^+$

DESCRIPTION 15

7-Amino-1,1,2-trimethyl-1,2,3,4-tetrahydroisoquinoline

7-Amino-1,2-dimethyl-3,4-dihydroisoquinolinium iodide (1.44 g, 4.8 mmol) was suspended in THF (200 ml), cooled to −78° C. and treated with methyl magnesium chloride (10 ml of a 3M solution in THF) added as a single portion. The reaction was allowed to reach room temperature over 18 h and poured into water (200 ml). The organic solvent was removed in vacuo and the resultant oily residue extracted into dichloromethane (3×50 ml). Evaporation in vacuo and chromatography through silica gel eluting with (0.5% 0.88 NH$_3$: 4.5% CH$_3$OH: 95% CH$_2$Cl$_2$) yielded the title compound as a yellow oil (0.07 g, 8%). For ease of handling the product was converted into a monohydrochloride.

$^1$H NMR (250 MHz, CDCl$_3$) δ: 1.45 (6H, s), 2.48 (3H, s), 2.80 (2H, t, J=6 Hz), 2.96 (2H, t, J=6 Hz), 6.51 (1H, dd, J=8, 2 Hz), 6.57 (1H, d, J=2 Hz), 6.86 (1H, d, J=8 Hz).

PREPARATION 1

Methyl 3-Chloro-4-iso-propoxybenzoate

Methyl 3-chloro-4-hydroxybenzoate (5 g, 26.8 mmol) in DMF (45 ml) was treated with potassium carbonate (7.41 g, 53.6 mmol), 2-iodopropane (3.85 ml, 40.2 mmol) and then stirred at 25° C. for 18 h. Work-up with ethyl acetate gave the title compound (6.1 g).

PREPARATION 2

3-Chloro-4-iso-propoxybenzoic acid

Methyl 3-chloro-4-isopropoxybenzoate (5.5 g, 24.1 mmol) was hydrolysed using 1M NaOH (36 ml) in methanol (80 ml). Extraction and work-up with ethyl acetate gave the title compound (4.3 g).

$^1$H NMR (DMSO) δ: 1.33 (6H, d), 4.79 (1H, m), 7.24 (5H, d), 7.87 (2H, m).

PREPARATION 3

3-Bromo-4-ethylbenzoic acid

The title compound was prepared from 4-ethylbenzoic acid in a manner similar to that of Procedure 1.

$^1$H NMR (DMSO) δ: 1.45 (3H, t, J=7 Hz), 4.26 (2H, q, J=7 Hz), 7.26 (1H, d, J=9 Hz), 7.98 (1H, dd, J=2, 9 Hz), 8.12 (1H, d, J=2 Hz).

PREPARATION 4

3-Bromo-4-ethylbenzoic acid

The title compound was prepared from 4-ethylbenzoic acid in a manner similar to that of Procedure 1.

$^1$H NMR (DMSO) δ: 1.20 (3H, t, J=7 Hz), 2.78 (2H, q, J=7 Hz), 7.50 (1H, d, J=8 Hz), 7.90 (1H, dd, J=2, 8 Hz), 8.07 (1H, d, J=8 Hz).

PREPARATION 5

3-Cyano-4-iso-propylbenzoic acid

The title compound was prepared from 4-iso-propylbenzoic acid using a manner similar to that described in Procedures 1 and 5.

$^1$H NMR (DMSO) δ: 1.07 (6H, d, J=7 Hz), 3.13 (1H,m, overlapped), 7.48 (1H, d, J=7 Hz), 7.96 (1H, dd, J=2, 8 Hz)), 8.00 (1H, d, J=2 Hz).

PREPARATION 6

4-Methoxy-3-trifluoromethylbenzoic acid

The title compound was prepared from 3-bromo-4-methoxybenzoic acid and potassium trifluoroacetate in a manner similar to that of Procedures 3 and 4.

$^1$H NMR (DMSO) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br,exchangeable).

PREPARATION 7

4-Methoxy-3-trifluoromethylbenzoyl chloride

The title compound was prepared from 4-methoxy-3-trifluoromethylbenzoic acid with oxalkyl chloride and DMF in chloroform at room temperature followed by evaporation in vacua.

PROCEDURE 1

5-Bromo-2,4-dimethoxybenzoic acid

To a solution of 2,4-dimethoxybenzoic acid (4.0 g, 0.022 mol) in chloroform (60 ml) was added bromine (1.13 ml, 0.022 mol) in chloroform (20 ml) dropwise. After stiring overnight at room temperature the precipitate was filtered off and dried to afford the title compound as a white solid (2.87 g).

PROCEDURE 2

5-Bromo-4-iso-propyl-2-methoxybenzoic acid

To a solution of 2-methoxy-4-iso-propyl benzoic acid (7.0 g, 36.0 mmol) in chloroform (100 ml) was added bromine (1.86 ml) in chloroform (20 ml) dropwise. The reaction was stirred at room temperature overnight Evaporation in vacuo afforded an oil (9.27 g). m/z (CI): 275, 273 (MH$^+$; 70%).

PROCEDURE 3

Methyl-5-bromo-4-iso-propyl-2-methoxy benzoate

5-Bromo-4-iso-propyl-2-methoxybenzoic acid (9.268 g 34.0 mmol) was dissolved in ethanol (250 ml) and conc. H$_2$SO$_4$ (2 ml) added. The mixture was refluxed for 5 h and concentrated in vacuo. Residual material was taken up into ethyl acetate and water, and the organic layer, dried (MgSO$_4$). Concentration in vacuo afforded an oil, which was purified by Biotage Column Chromatography on silica gel using 10% ether in hexane to give an oil (5.5 g).

PROCEDURE 4

2,4-Dimethoxy-5-trifluoromethylbenzoic acid 2,4-Dimethoxy-5-bromobenzoic acid methyl ester (1.5 g; 5.4 mmol) in DMF (25 ml) and toluene (8 ml) under argon was treated with potassium trifluoroacetate (1.53 g; 10.1 mmol) and copper (I) iodide (2.1 g, 10.9 mmol). The mixture was heated to 170° C. with removal of water (Dean/Stark), and then at 155° C. overnight. The mixture was allowed to cool, poured into ether and water and filtered through Kieselguhr. The organic layer was dried (Na$_2$SO$_4$) and concentrated in vacuo to give a brown solid. Chromatography on Kieselgel 60 with 1:1 ether/petrol gave a white solid (1.03 g) which was hydrolysed in 1:1 methanolic: aqueous NaOH (50 ml) at 50° C. Work-up gave the title compound as a white solid (1 g).

PROCEDURE 5a

Methyl 2-methoxy-5-cyano-4-iso-propylbenzoate

Copper (I) cyanide (550 mg, 6 mmol) was added to a solution of methyl 2-methoxy-5-bromro-4-iso-propylbenzoate (861 mg) in N-methyl-2-pyrolidinone (30 ml). The mixture was stirred under argon and boiled under reflux for 4 h. The mixture was cooled, poured into excess ice/water and ethyl acetate and filtered. The organic phase was separated, washed with water, brine and dried(MgSO$_4$). Evaporation gave a crude brown solid which was purified by chromatography on silica gel eluting with ethyl acetate/n-hexane (1:4). The product was obtained as a white solid (523 mg).

$^1$H NMR (250 MHz, CDCl$_3$) δ: 1.33 (6H, d, J=7 Hz), 3.38 (1H, sep, J=7 Hz), 3.89 (3H, s), 3.98 (3H, s), 6.91 (1H, s), 8.08 (1H, s); m/z (API$^+$): 234 (MH$^+$, 30%).

PROCEDURE 5b

2-Methoxy-5-cyano-4-iso-propylbenzoic acid

2N NaOH (1–25 ml) was added to a solution of the methyl ester P5a (490 mg) in methanol (10 ml). The solution was stirred overnight at room temperature. The solution was then diluted with water, concentrated in vacuo and washed with ethyl acetate. The aqueous phase was then acidified with 2N HCl and extracted with ethyl acetate. The extract was washed with brine, dried (MgSO$_4$) and evaporated to dryness giving the product as a white solid (418 mg).

$^1$H NMR (250 MHz, CDCl$_3$) δ: 1.35 (6H, d, J=7 Hz), 3.43 (1H, sep, J=7 Hz), 4.14 (3H,s), 7.00 (1H, s), 8.41 (1H, s); m/z (API$^+$): 220 (MH$^+$, 100%).

PROCEDURE 6a

Ethyl 2-ethoxy-4-iso-propyl-5-cyanobenzoate

Ethyl 2-ethoxy-4-iso-propyl-5-bromobenzoate (1.2 g, 3–8 mmol) was treated with copper (I) cyanide (682 mg, 7.6 m.mol) in N-methyl-2-pyrrolidinone (40 ml) as described in Procedure 5 to give the title compound as an oil (400 mg).

$^1$H NMR (250 MHz, CDCl$_3$) δ: 1.12 (6H, d, J=7 Hz), 1.30 (3H, t, J=7 Hz), 1.84 (3H, t, J=7 Hz), 3.17 (1H, sep, J=7 Hz), 3.99 (2H, q, J=9 Hz), 4.16 (2H, q, J=7 Hz), 6.69 (1H, s), 7.86 (1H, s); m/z (API$^+$): 262 (MH$^+$, 100%).

PROCEDURE 6b

2-Ethoxy-4-iso-propyl-5-cyanobenzoic acid

The ester P6a (370 mg, 1.41 mmol) was dissolved in methanol (5 ml) and over a 24 h period 1N NaOH (2.1 ml, 2.1 mmol) was added. The solution was concentrated under vacuum, diluted with water and washed with ethyl acetate. The aqueous phase was acidified with 2N HCl and extracted with ethyl acetate. The extract was washed with brine, dried (MgSO$_4$) and evaporated to give the title acid (306 mg).

$^1$H NMR (250 MHz CDCl$_3$) δ: 1.39 (3H, d, J=7 Hz), 1.66 (3H, t, J=7 Hz), 3.47 (1H, sep, J=7 Hz), 4.46 (2H, q, J=7 Hz), 7.03 (1H, s), 8.47 (1H, s); m/z (API$^+$): 234 (MH$^+$, 100%).

PROCEDURE 7

4-Ethoxy-2-methoxy-5-methylsulfonylbenzoic acid

4-Ethoxy-2-methoxy-5-chlorosulfonyl benzoic acid in a 49% yield. was prepared in 49% yield using the procedure of M. W. Harrold et al., J. Med. Chem., 1989, 32 874. This was used according to the method of R. W. Brown, J. Org. Chem., 1991, 56, 4974, to the title compound in 19% yield.

$^1$H NMR (DMSO) δ: 1.30 (3H, t), 3.10 (3H, s), 3.83 (3H, s), 4.24 (2H, q), 6.73 (1H, s), 8.07 (1H, s).

PROCEDURE 8

4-iso-Propyl-2-methoxy-5-methylsulfonylbenzoic acid

This was prepared in a similar manner to the procedure of C. Hansch, B. Schmidhalter, F. Reiter, W. Saltonstall. J. Org. Chem., 1956, 21, 265 to afford the intermediate 5-chlorosulfonyl-4-isopropyl-2-methoxybenzoic acid which was converted into the title compound using the method of Procedure 7.

$^1$H NMR (DMSO) δ: 1.30 (6H, d), 3.21 (3H, s), 3.80 (1H, m), 3.94 (3H, s), 7.26 (1H, s), 8.19 (1H, s).

EXAMPLE 1

(a) (±) 2-(t-Butoxycarbonyl)-N-(1-methyl-1,2,3,4-tetrahydroisoquinolin-5-yl)-5-chloro-4-ethoxy-2-methoxybenzamide To a solution of 5-amino-2-(t-butoxycarbonyl)-1-methyl-1,2,3,4-tetrahydro-isoquinoline (0.251 g, 0.9 mmol) in dichloromethane (8 ml) and triethylamine (0.75 ml) was added 5-chloro-4-ethoxy-2-methoxybenzoyl chloride (0.262 g, 1.05 mmol) and the mixture stirred at room temperature overnight After diluting with more dichloromethane, the mixture was washed with sodium bicarbonate solution. The organic layer was dried over sodium sulfate and concentrated in vacuo to afford a beige solid. This was then recrystalised from ethyl acetate and petrol to afford a white solid. (0.124 g).

(b) (±) N-(1-Methyl-1,2,3,4-tetrahydroisoquinolin-5-yl)-5-chloro-4-ethoxy-2-methoxybenzamide, trifluoroacetate To a solution of the above boc protected compound (0.124 g, 0.47 mmol) in dichloromethane (5 ml) at 0° C. was added trifluoroacetic acid (0.37 ml) dropwise. The solution was stirred at room temperature for 3 h and then the solvent was removed in vacuo to afford a beige solid (0.192 g).

$^1$H NMR (DMSO-d$^6$) δ: 1.42 (3H, t, J=6 Hz), 1.60 (3H, d, J=6 Hz), 2.94 (2H, m), 3.48 (2H, m), 4.08 (3H, s), 4.28 (2H, m), 6.95 (1H, s), 7.19 (1H, d, J=6 Hz), 7.32 (1H, t, J=6 Hz), 7.28 (1H, d, J=6 Hz), 7.48 (1H, s), 9.00 (1H, m), 9.30 (1H, m), 9.73 (1H, s); m/z (CI): 375 (MH$^+$)

EXAMPLE 2

(±) N-(1,2-Dimethyl-1,2,3,4-tetrahydroisoquinolin-5-yl)-5-bromo-2,4-dimethoxybenzamide, hydrochloride The title compound was prepared in a similar fashion to Example 1 from 5-amino-1,2-dimethyl-1,2,3,4-tetrahydroisoquinoline and 2,4-dimethoxy-5-bromobenzoic acid. The crude product was recrystallised from methanol and ethyl acetate to afford a white solid (101 mg).

$^1$H NMR (DMSO-d$^6$) δ: 1.62 (3H, m), 2.85 (3H, br.s), 3.00 (2H, m), 3.18 (2H, s), 4.02 (3H, s), 4.12 (3H, s), 4.63 (1H, m), 6.93 (1H, s), 7.15 (1H, d, J=6 Hz), 7.35 (1H, t, J=6 Hz), 7.88 (1H, d, J=6 Hz), 8.09 (1H, s), 9.75 (1H, s), 10.91 (1H, br.s); m/z (CI): 419 (MH$^+$)

EXAMPLE 3

(±) N-(1,2-Dimethyl-1,2,3,4-tetrahydroisoquinolin-5-yl)-5-chloro-4-ethoxy-2-methoxybenzamide, hydrochloride The title compound was prepared in a similar fashion to Example 1 from 5-amino-1,2-dimethyl-1,2,3,4-tetrahydroisoquinoline and 5-chloro-4-ethoxy-2-methoxybenzoic acid. The crude product was recrystallised from methanol and ethyl acetate to afford a pale brown solid (319 mg).

$^1$H NMR (DMSO-d$^6$) δ: 1.42 (3H, t, J=6 Hz), 1.56 (1H, d, J=6 Hz), 1.70 (2H, d, J=6 Hz) 2.80 (2H, m), 3.03 (2H, m), 3.32–3.62 (3H, m), 4.09 (3H, s), 4.29 (2H, m), 4.65 (1H, m), 6.96 (1H, s), 7.12 (1H, m), 7.35 (1H, t, J=6 Hz), 7.90 (2H, m), 9.25 (1H, m), 11.42 (1H, br.s); m/z (CI): 389 (MH$^+$)

The following Examples were prepared using methods similar to those outline above.

EXAMPLE 4

(±) N-(1,2-Dimethyl-1,2,3,4-tetrahydroisoquinolin-5-yl)-5-chloro-4-iso-propoxy-2-methoxybenzamide, hydrochloride $^1$H NMR (DMSO-d$^6$) δ: 1.32 (6H, d), 1.6 (3H, m), 2.66 (3H, m), 3.02 (2H, m), 3.58 (2H, m), 4.04 (3H, s), 4.60 (1H, m), 4.97 (1H, m), 7.17–7.90 (5H, m), 9.75 (1H, m), 11.30 (1H, br s); m/z (CI): 403 (MH$^+$).

EXAMPLE 5

(±) N-(1,2-Dimethyl-1,2,3,4-tetrahydroisoquinolin-5-yl)-tert-butyl-2-methoxybenzamide, hydrochloride $^1$H NMR (DMSO-d$^6$) δ: 1.32 (9H, s), 1.61 (3H, m), 2.82 (3H, m), 3.07 (2H, m), 3.50 (2H, m), 4.05 (3H, s), 4.64 (1H, m), 7.12 (3H, m), 7.34 (1H, m), 7.88 (2H, m), 9.85 (1H, br s), 11.08 (1H, br s); m/z (CI): 367 (MH$^+$).

EXAMPLE 6

(±) N-(1,2-Dimethyl-1,2,3,4-tetrahydroisoquinolin-5-yl)-5-trifluoromethyl-2-methoxy-4-methyl benzamide, hydrochloride $^1$H NMR (DMSO-d$^6$) δ: 1.60 (4H, m), 2.80 (4H, m), 3.00 (2H, m), 3.50 (3H, m), 4.06 (3H, s), 4.55 (1H, m), 7.20 (3H, m), 7.73 (1H, m), 8.08 (1H, m), 9.81 (1H, m), 11.27 (1H, m); m/z (CI): 393 (MH$^+$).

EXAMPLE 7

N-(2,4,4-Trimethyl-4H-isoquinolin-7-yl)-4-methoxy-3-trifluoromethylbenzamide, hydrochloride The amine hydrochloride D8 (226 mg, 1.0 mmol) in dichloromethane (10 ml) was sequentially treated with 4-methoxy-3-trifluoromethylbenzoyl chloride (283 mg, 1.0 mmol) and triethylamine (0.4 ml, 2.9 mmol). The mixture was stirred at 25° C. for 18 h and evaporated in vacuo. The resultant residue was purified by chromatography on silica gel eluting with dichloromethane:ammonia:methanol (0.5% conc. ammonia: 4.5% methanol: 95% dichloromethane). The title compound was obtained as an off-white foam (337 mg, 86%) which was converted into the hydrochloride.

$^1$H NMR (250 MHz, d$^6$DMSO) δ: 1.26 (3H, s), 1.37 (3H, s), 2.43 (5H, overlapping DMSO), 3.91 (3H, s), 4.30 (2H, m), 7.36 (1H, d, J=9 Hz), 7.42 (1H, d, J=9 Hz), 7.58 (2H, m), 8.18 (1H, s), 8.23 (1H, d, J=9 Hz), 9.80 (1H, brs); m/z (API$^+$): 393 (M+H)$^+$

EXAMPLE 8

N-(2,4,4-Trimethyl-4H-isoquinolin-7-yl)-3-cyano-4-iso-propylbenzamide

Prepared in a similar manner to Example 7, using 3-cyano-4-iso-propylbenzoyl chloride, and isolated in 70% yield.

$^1$H NMR (250 MHz, CDCl$_3$) δ: 1.31 (6H, s), 1.35 (6H, d, J=7 Hz), 2.40 (2H, s), 2.42 (3H, s), 3.44 (1H, m), 3.55 (2H, s), 7.37 (3H, s), 7.53 (1H, d, J=8 Hz), 7.67 (1H, brs), 8.02 (1H, d, J=2 Hz), 8.09 (1H, d, J=2 Hz); m/z (API$^+$): 362 (M+H)$^+$

EXAMPLE 9

N-(2,4,4,-Trimethyl-4H-isoquinolin-7-yl)-3-bromo-4-ethylbenzamide

Prepared in a similar manner to Example 7, using 3-bromo-4-ethylbenzoyl chloride, and isolated in 89% yield.

$^1$H NMR (250 MHz, CDCl$_3$) δ: 1.26 (3H, t, J=8 Hz), 1.30 (6H, s), 2.39 (2H, s), 2.42 (3H, s), 2.82 (2H, q, J=8 Hz), 3.54 (2H, s), 7.37 (3H, m), 7.51 (1H, d, J=2 Hz), 7.80 (1H, brs), 8.03 (1H, br s); m/z (API$^+$): 402, 404 (M+H)$^+$

EXAMPLE 10

N-(2,4,4-Trimethyl-4H-isoquinolin-7-yl)-3-bromo-4-ethoxybenzamide

The amine hydrochloride D8 (226 mg, 1.0 mmol) in dichloromethane (10 ml) was sequentially treated with 3-bromo-4-ethoxybenzoyl chloride, (270 mg, 1.0 mmol) and triethylamine (0.4 ml, 2.9 mmol). The mixture was stirred at 25° C. for 18 h and evaporated in vacuo. The resultant residue was purified by chromatography on silica gel eluting with ammonia:methanol:dichloromethane (0.5% 0.88 ammonia: 4.5% methanol: 95% dichloromethane). The title compound was obtained as an off-white foam (291 mg, 70%).

$^1$H NMR [free base](250 MHz, CDCl$_3$) δ: 1.30 (6H, s), 1.51 (3H, t, J=7 Hz), 2.39 (2H, s), 2.41 (3H, s), 3.53 (2H, s), 4.17 (2H, q, J=7 Hz), 6.93 (1H, d, J=9 Hz), 7.34 (3H, m), 7.65 (1H, brs), 7.80 (1H, dd, J=9, 2 Hz), 8.04 (1H, d, J=2 Hz); m/z (API$^+$): 418, 420 (M+H)$^+$ A portion of the title compound was converted into the hydrochloride salt.

$^1$H NMR (250 MHz, d$^6$-DMSO) δ: 1.21 (3H, s), 1.28 (3H, t, J=7 Hz), 1.34 (3H, s), 2.34–2.44 (2H, brs), 2.83 (3H, d, J=4 Hz), 4.10 (2H, q, J=7 Hz), 4.15–4.37 (2H, m), 7.13 (1H, d, J=9 Hz), 7.37 (1H, d, J=8 Hz), 7.52 (1H, brs), 7.54 (1H, d, J=9 Hz),), 7.89 (1H, dd, J=9, 2 Hz), 8.12 (1H, d, J=2 Hz),), 10.18 (1H, s), 10.35 (1H, brs).

EXAMPLE 11

N-(2,4,4-Trimethyl-4H-isoquinolin-7-yl)-3-chloro--4-iso-propoxybenzamide

Prepared in a similar manner to Example 7, using 3-chloro-4-iso-propoxybenzoyl chloride, and isolated in 84% yield.

$^1$H NMR (250 MHz, CDCl$_3$) δ: 1.30 (6H, s), 1.42 (6H, d, J=6 Hz), 2.39 (2H, s), 2.41 (3H, s), 3.53 (2H, s), 4.66 (1H, septet, J=6 Hz), 6.98 (1H, d, J=9 Hz), 7.35 (3H, m), 7.68 (1H, brs), 7.74 (1H, dd, J=9, 2 Hz), 7.87 (1H, d, J=2 Hz). m/z (API$^+$): 387, 389 (M+H)$^+$

EXAMPLE 12

(±) N-(1,2-Dimethyl-4H-isoquinolin-7-yl)-3-bromo-4-ethylbenzamide (±) 7-Amino-1,2-dimethyl-tetrahydroisoquinoline mono hydrochloride (0.106 g, 0.50 mmol) in dichloromethane (10 ml) was sequentially treated with 3-bromo-4-ethylbenzoyl chloride (0.124 g, 0.50 mmol) and triethylamine (0.3 ml, 2.2 mmol). The mixture was stirred at ambient temperature for 18 h. Evaporation in vacuo gave an oily residue which was purified by chromatography through silica gel eluting with (0.5% conc. ammonia: 4.5% methanol: 95% dichloromethane). The title compound was obtained as an off-white foam (0.149 g, 77%).

$^1$H NMR (250 MHz, CDCl$_3$) δ: 1.23 (3H, t, J=8 Hz), 1.36 (3H, d, J=7 Hz), 2.46 (3H, s), 2.60(1H, m), 2.80 (4H, m), 3.54 (1H, q, J=7 Hz), 7.02 (1H, d, J=8 Hz), 7.25 (1H, d, J=8 Hz), 7.32 (1H, dd, J=8, 2 Hz), 8.00 (1H, d, J=2 Hz), 8.17 (1H, s); m/z (API): 387, 389 (M+H)$^+$

EXAMPLE 13

(±) (N-(1,2-Dimethyl-4H-isoquinolin-7-yl)-3-bromo-4-ethoxybenzamide

Prepared as described in Example 12 using 3-bromo-4-ethoxybenzoyl chloride and isolated in 90% yield.

$^1$H NMR (250 MHz, CDCl$_3$) δ: 1.36 (3H, d, J=7 Hz), 1.49 (3H, t, J=7 Hz), 2.46 (3H, s), 2.64 (1H, m), 2.80 (2H, m), 3.00 (1H, m), 3.55 (1H, q, J=7 Hz), 4.13 (2H, q, J=7 Hz), 6.85 (1H, d, J=9 Hz), 7.02 (1H, d, J=8 Hz), 7.32 (1H, d, J=8, 2 Hz), 7.45 (1H, s), 7.77 (1H, dd, J=9, 2 Hz), 8.06 (1H, s), 8.08 (1H, d, J=2 Hz); m/z (API): 403, 405 (M+H)$^+$

EXAMPLE 14

N-(1,1,2-Trimethyl-4H-isoquinolin-7-yl)-4-methoxy-3-trifluoromethylbenzamide

The title compound was prepared from 7-amino-1,1,2-trimethyl-tetrahydroisoquinoline mono hydrochloride (0.077 g, 0.3 mmol) and 3-trifluoromethyl-4-methoxybenzoyl chloride (0.083 g, 0.3 mmol) in a manner similar to that of Example 12 as an off-white foam (0.132 g, 99%).

$^1$H NMR(250 MHz, CDCl$_3$) δ: 1.40 (6H, s), 2.44 (3H, s), 2.78–2.93 (4H, m), 3.95 (3H, s), 7.00 (1H, s), 7.03 (1H, s), 7.33 (1H, dd, J=8, 2 Hz), 7.59 (1H, d, J=2 Hz), 8.03–8.10 (3H, m); m/z (API): 393 (M+H)$^+$

PHARMACOLOGICAL DATA

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test. For example, compounds of Examples 1 to 14 gave pKi values greater than 7.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Results

Compounds of this invention dosed at 10 mg/kg by the oral route as a suspension in methyl cellulose and tested one hour post dosing showed an increase in seizure threshold. At a dose of 10 mg/kg/p.o. at 2 h, the compounds of Examples 4, 5, and 6 showed percentage increases of 47, 46, and 36% respectively.

Method for Rat Model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration; from 1–300 mA in steps of 5–20 mA). The procedure is similar to that outlined above for mouse and full details are as published by Upton et al,.[4]

The percentage increase or decrease in $CC_{50}$ for each group compared to the control is calculated.

Drugs are suspended in 1% methyl cellulose.

Results

At a dosage of 2 mg/kg p.o. at 2 h, the compounds of Examples 7 to 11 show the increases set out in the Table.

TABLE

| Ex No | pKI Compound A | Rat MEST at 2 mg/kg p.o at 2h |
|---|---|---|
| E7 | 8.5 | 510 |
| E8 | 8.0 | 120 |
| E9 | 8.3 | 53 |
| E10 | 8.2 | 294 |
| E11 | 7.9 | 204 |

References

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113
4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M. Thompson. (1997). B. J. Pharmacol., 121, 1679–1686

What is claimed is:

1. A compound ot formula (I) or pharmaceutically acceptable salt thereof:

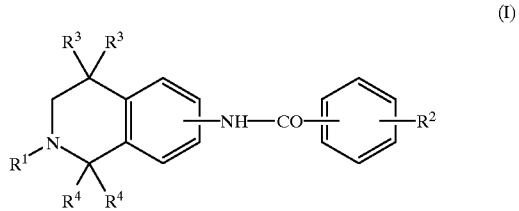

where $R^1$ is hydrogen, $C_{1-6}$ alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—, $R^2$ is hydrogen or up to three substituents selected from halogen, $NO_2$, CN, $N_3$, $CF_3O$—, $CF_3S$—, $CF_3CO$—, trifluoromethyldiazirinyl, $C_{1-6}$alkyl, $C_{1-6}$alkenyl, $C_{1-6}$alkynyl, $C_{1-6}$perfluoroalkyl, $C_{3-6}$-cycloalkyl, $C_{3-6}$-cycloalkyl-$C_{1-4}$alkyl-, $C_{1-6}$alkylO—, $C_{1-6}$alkylCO—, $C_{3-6}$-cycloalkylO—, $C_{3-6}$-cycloalkylCO—, $C_{3-6}$-cycloalkyl-$C_{1-4}$alkylO—, $C_{3-6}$-cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl$)$NHSO$_2$—, $(C_{1-4}$alkyl$)_2$NCO—, $(C_{1-4}$alkyl$)$NHCO— or CONH$_2$;

or —NR$^5$R$^6$ where R$^5$ is hydrogen or $C_{1-4}$ alkyl, and R$^6$ is hydrogen, $C_{1-4}$alkyl, formyl, —CO$_2$C$_{1-4}$alkyl or —COC$_{1-4}$alkyl or two R$^2$ groups together form a carbocyclic ring that is saturated or unsaturated and unsubstituted or substituted by —OH or =O; and the two R$^3$ groups and the two R$^4$ groups are each independently hydrogen or $C_{1-6}$ alkyl or the two R$^3$ groups and/or the two R$^4$ groups together form a $C_{3-6}$ spiroalkyl group provided that at least one R$^3$ or R$^4$ group is not hydrogen;

provided that the compound is not 1-methyl-6-benzoylamino-1,2,3,4-tetrahydroisoquinoline, or 1,2-dimethyl-6-benzoylamino-1,2,3,4-tetrahydroisoquinoline.

2. A compound according to claim 1 which has the formula (IA)

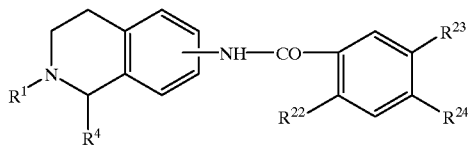

(IA)

where

R$^1$ is hydrogen, $C_{1-6}$ alkyl (optionally substituted by hydroxy or $C_{1-4}$alkoxy), $C_{1-6}$ alkenyl, $C_{1-6}$ alkynyl, formyl, $C_{1-6}$alkylCO, $C_{1-6}$alkylSO$_2$, or CF$_3$CO—;

R$^{22}$ is $C_{1-6}$alkylO—, $C_{3-6}$cycloalkylO— or $C_{3-6}$-cycloalkyl $C_{1-4}$alkylO—;

R$^{23}$ is hydrogen, halogen, CN, N$_3$, trifluoromethyldiazirinyl, $C_{1-6}$perfluoroalkyl, CF$_3$O—, CF$_3$S—, CF$_3$CO—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$, $(C_{1-4}$alkyl$)$NHSO$_2$, $(C_{1-4}$alkyl$)_2$NCO—, $(C_{1-4}$alkyl$)$NHCO— or CONH$_2$;

R$^{24}$ is hydrogen, halogen, NO$_2$, CN, N$_3$, trifluoromethyldiazirinyl, $C_{1-6}$ alkylO—, $C_{1-6}$alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, CF$_3$CO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-;

or —NR$^5$R$^6$ where R$^5$ is hydrogen or $C_{1-4}$ alkyl, and R$^6$ is hydrogen, $C_{1-4}$alkyl, formyl, —CO$_2$C$_{1-4}$alkyl or —COC$_{1-4}$alkyl;

or R$^{23}$ and R$^{24}$ together form a carbocyclic ring that is unsaturated or saturated and unsubstituted or substituted by carbonyl or hydroxyl;

R$^4$ is $C_{1-6}$ alkyl.

3. A compound according to claim 1 which has the formula (IB)

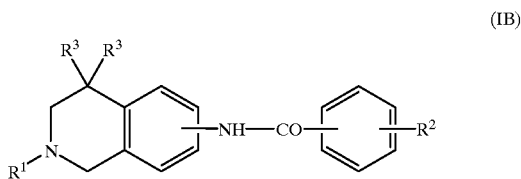

(IB)

where R$^1$ is hydrogen, $C_{1-6}$ alkyl (optionally substituted by hydroxy or $C_{1-4}$alkoxy), $C_{1-6}$alkenyl, $C_{1-6}$alkynyl, $C_{1-6}$alkylCO—, formyl, CF$_3$CO— or $C_{1-6}$alkylSO$_2$—, R$^2$ is hydrogen or up to three substituents selected from halogen, NO$_2$, CN, N$_3$, CF$_3$O—, CF$_3$S—, CF$_3$CO—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)$NSO$_2$—, $(C_{1-4}$alkyl$)$NHSO$_2$—, $(C_{1-4}$alkyl$)_2$NCO—, $(C_{1-4}$alkyl$)$NHCO— or CONH$_2$;

or —NR$^5$R$^6$ where R$^5$ is hydrogen or $C_{1-4}$ alkyl, and R$^6$ is hydrogen, $C_{1-4}$alkyl, formyl, —CO$_2$C$_{1-4}$alkyl or —COC$_{1-4}$alkyl;

or two R$^2$ groups together form a carbocyclic ring that is saturated or unsaturated and unsubstituted or substituted by —OH or =O; and each R$^3$ is $C_{1-6}$ alkyl.

4. A compound according to claim 1 which has formula (IC)

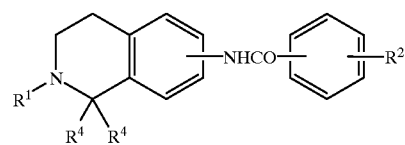

(IC)

where R$^1$ is hydrogen, $C_{1-6}$ alkyl (optionally substituted by hydroxy or $C_{1-4}$alkoxy), $C_{1-6}$alkenyl, $C_{1-6}$alkynyl, $C_{1-6}$alkylCO—, formyl, CF$_3$CO— or $C_{1-6}$alkylSO$_2$—, R$^2$ is hydrogen or up to three substituents selected from halogen, NO$_2$, CN, N$_3$, CF$_3$O—, CF$_3$S—, CF$_3$CO—, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl$)$NHSO$_2$—, $(C_{1-4}$alkyl$)_2$NCO—, $(C_{1-4}$alkyl$)$NHCO— or CONH$_2$;

or —NR$^5$R$^6$ where R$^5$ is hydrogen or $C_{1-4}$ alkyl, and R$^6$ is hydrogen, $C_{1-4}$alkyl, formyl, —CO$_2$C$_{1-4}$alkyl or —COC$_{1-4}$alkyl;

or two R$^2$ groups together form a carbocyclic ring that is saturated or unsaturated and unsubstituted or substituted by —OH or =O; and each R$^4$ is $C_{1-6}$ alkyl.

5. A compound according to claim 1 selected from the group consisting of:

(±) N-(1-methyl-1,2,3,4-tetrahydroisoquinolin-5-yl-
  5chloro-4-ethoxy-2-methoxybenzamide
(±) N-(1,2-dimethyl-1,2,3,4-tetrahydroisoquinolin-5-yl)-
  5-bromo-2,4-dimethoxybenzamide
(±) N-(1,2-dimethyl-1,2,3,4-tetrahydroisoquinolin-5-yl)-
  5-chloro-4-ethoxy-2-methoxybenzamide
(±) N-(1,2-dimethyl-1,2,3,4-tetrahydroisoquinolin-5-yl)-
  5-chloro-4-iso-propoxy-2-methoxybenzamide
(±) N-(1,2-dimethyl-1,2,3,4-tetrahydroisoquinolin-5-yl)-
  4-tert-butyl-2-methoxybenzamide
(±) N-(1,2-dimethyl-1,2,3,4-tetrahydroisoquinolin-5-yl)-
  5-trifluoromethyl-2-methoxy-4-methyl-benzamide
N-(2,4,4-trimethyl-4H-isoquinolin-7-yl)-4-methoxy-3-
  trifluoromethylbenzamide
N-(2,4,4-trimethyl-4H-isoquinolin-7-yl)-3-cyano-4-iso-
  propylbenzamide
N-(2,4,4,-trimethyl-4H-isoquinolin-7-yl)-3-bromo-4-
  ethylbenzamide
N-(2,4,4-trimethyl-4H-isoquinolin-7-yl)-3-bromo-4-
  ethoxybenzamide
N-(2,4,4-trimethyl-4H-isoquinolin-7-yl)-3-chloro-4-iso-
  propoxybenzamide
(±) N-(1,2-dimethyl-4H-isoquinolin-7-yl)-3-bromo-4-
  ethylbenzamide
(±) N-(1,2-dimethyl-4H-isoquinolin-7-yl)-3-bromo-4-
  ethoxybenzamide
N-(1,1,2-trimethyl-4H-isoquinolin-7-yl)-4-methoxy-3-
  trifluoromethylbenzamide.

6. A process for the preparation of compounds according to claim 1 which comprises reacting a compound of formula (II)

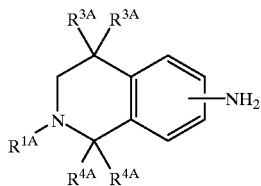
(II)

where $R^{1A}$, $R^{3A}$, $R^{4A}$ are $R^1$, $R^3$, $R^4$ as defined for formula (I) or a group or groups convertible to $R^1$, $R^3$, $R^4$
with a compound of formula (III)

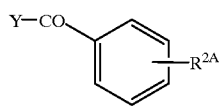
(III)

where Y is Cl or OH, and $R^{2A}$ groups are independently $R^2$ as defined for formula (I) or a group or groups convertible to $R^2$,
and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

7. A process for the preparation of compounds according to claim 2 which comprises reacting a compound of formula (II)

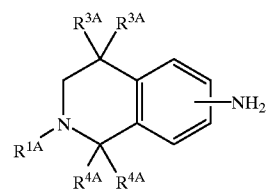
(II)

where $R^{1A}$, $R^{3A}$, $R^{4A}$ are $R^1$, $R^3$, $R^4$ as defined for formula (I) or a group or groups convertible to $R^1$, $R^3$, $R^4$
with a compound of formula (III)

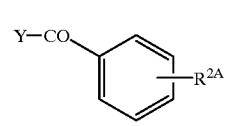
(III)

where Y is Cl or OH, and $R^{2A}$ groups are independently $R^2$ as defined for formula (I) or a group or groups convertible to $R^2$,
and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

8. A process for the preparation of compounds according to claim 3 which comprises reacting a compound of formula (II)

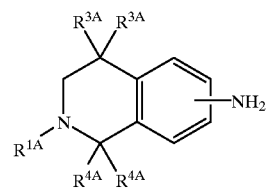
(II)

where $R^{1A}$, $R^{3A}$, $R^{4A}$ are $R^1$, $R^3$, $R^4$ as defined for formula (I) or a group or groups convertible to $R^1$, $R^3$, $R^4$
with a compound of formula (III)

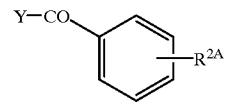
(III)

where Y is Cl or OH, and $R^{2A}$ groups are independently $R^2$ as defined for formula (I) or a group or groups convertible to $R^2$,
and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

9. A process for the preparation of compounds according to claim 4 which comprises reacting a compound of formula (II)

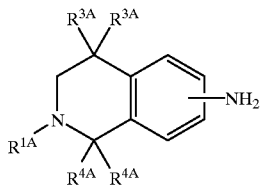

(II)

where $R^{1A}$, $R^{3A}$, $R^{4A}$ are $R^1$, $R^3$, $R^4$ as defined for formula (I) or a group or groups convertible to $R^1$, $R^3$, $R^4$ with a compound of formula (III)

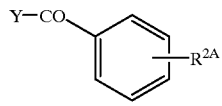

(III)

where Y is Cl or OH, and $R^{2A}$ groups are independently $R^2$ as defined for formula (I) or a group or groups convertible to $R^2$,
and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

10. A process for the preparation of compounds according to claim 5 which comprises reacting a compound of formula (II)

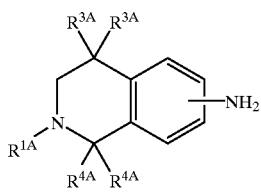

(II)

where $R^{1A}$, $R^{3A}$, $R^{4A}$ are $R^1$, $R^3$, $R^4$ as defined for formula (I) or a group or groups convertible to $R^1$, $R^3$, $R^4$ with a compound of formula (III)

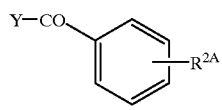

(III)

where Y is Cl or OH, and $R^{2A}$ groups are independently $R^2$ as defined for formula (I) or a group or groups convertible to $R^2$,
and where required converting an $R^{1A}$, $R^{2A}$, $R^{3A}$, $R^{4A}$ group to a $R^1$, $R^2$, $R^3$, $R^4$ group, converting one $R^1$, $R^2$, $R^3$, $R^4$ group to another $R^1$, $R^2$, $R^3$, $R^4$ group, or converting a salt product to the free base or another pharmaceutically acceptable salt, or separating any enantiomers, or converting a free base product to a pharmaceutically acceptable salt.

11. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 1 and a pharmaceutically acceptable carrier.

12. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 1.

13. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, triceminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 2 and a pharmaceutically acceptable carrier.

14. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 3 and a pharmaceutically acceptable carrier.

15. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 4 and a pharmaceutically acceptable carrier.

16. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 5 and a pharmaceutically acceptable carrier.

17. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 2.

18. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 3.

19. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 4.

20. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 5.

* * * * *